United States Patent [19]
King et al.

[11] Patent Number: 5,580,885
[45] Date of Patent: Dec. 3, 1996

[54] 5-HT$_4$ RECEPTOR ANTAGONISTS

[75] Inventors: Francis D. King; Laramie M. Gaster; Keith R. Mulholland; Shirley K. Rahman; Paul A. Wyman; Gareth J. Sanger; Kay A. Wardle; Gordon S. Baxter; Guy A. Kennett, all of Harlow; Alberto J. Kauman, Trumpington, all of England

[73] Assignee: SmithKline Beecham p.l.c., Brentford, England

[21] Appl. No.: 204,429

[22] PCT Filed: Sep. 9, 1992

[86] PCT No.: PCT/GB92/01649

§ 371 Date: Jul. 28, 1994

§ 102(e) Date: Jul. 28, 1994

[87] PCT Pub. No.: WO93/05038

PCT Pub. Date: Mar. 18, 1993

[30] Foreign Application Priority Data

| | | | |
|---|---|---|---|
| Sep. 12, 1991 | [GB] | United Kingdom | 9119449 |
| Sep. 14, 1991 | [GB] | United Kingdom | 9119692 |
| Oct. 23, 1991 | [GB] | United Kingdom | 9122473 |
| Oct. 23, 1991 | [GB] | United Kingdom | 9122474 |
| Oct. 24, 1991 | [GB] | United Kingdom | 9122624 |
| Jan. 23, 1992 | [GB] | United Kingdom | 9201413 |
| Jan. 23, 1992 | [GB] | United Kingdom | 9201414 |
| Feb. 6, 1992 | [GB] | United Kingdom | 9202510 |
| Jul. 7, 1992 | [GB] | United Kingdom | 9214399 |

[51] Int. Cl.$^6$ .................... A61K 31/445; A61K 31/44; C07D 405/12; C07D 455/02
[52] U.S. Cl. .................... 514/321; 514/306; 546/138; 546/197
[58] Field of Search .................... 546/138, 197; 514/306, 321

[56] References Cited

U.S. PATENT DOCUMENTS

| | | | |
|---|---|---|---|
| 4,186,135 | 1/1980 | Thominet | 514/321 |
| 4,268,512 | 5/1981 | Thominet | 514/321 |
| 4,499,099 | 2/1985 | Watts | 514/299 |
| 4,772,459 | 9/1988 | Sun | 514/321 |
| 5,185,335 | 2/1993 | Van Daele | 514/243 |

FOREIGN PATENT DOCUMENTS

| | | |
|---|---|---|
| 0036269 | 9/1981 | European Pat. Off. . |
| 0389037 | 10/1990 | European Pat. Off. . |
| 0407137 | 1/1991 | European Pat. Off. . |
| 2396757 | 2/1979 | France . |
| 2509155 | 9/1976 | Germany . |
| 2176785 | 1/1987 | United Kingdom . |
| 10454 | 6/1992 | WIPO . |
| 10089 | 5/1993 | WIPO . |

OTHER PUBLICATIONS

Witaker–Azmitia et al. "The neuropharmacology of Serotonin" N.Y. Academy of Science, 600 p. 195–196 (1990).
Clark et al. "Principles of Psychopharmacology" Academic Press, p. 166–167 (1970).

*Primary Examiner*—Ceila Chang
*Attorney, Agent, or Firm*—Charles M. Kinzig; Stephen Venetianer; Edward T. Lentz

[57] ABSTRACT

The use of a compound of formula (I) or pharmaceutically acceptable salt thereof, in which $X_1$—$(CH_2)_x$—$X_2$ forms a 5–7 membered ring wherein: $X_1$ is O or S; $X_2$ is O, S, NR or NRCO wherein R is hydrogen or $C_{1-6}$alkyl; x is 1, 2 or 3; Y is O or NH; Z is sub-formula (a), (b) or (c) in the manufacture of a medicament for use in the treatment of gastrointestinal disorders, cardiovascular disorders and CNS disorders.

5 Claims, No Drawings

5-HT₄ RECEPTOR ANTAGONISTS

This application is a 371 of PCT/GB92/01649 filed Sep. 9, 1992.

This invention relates to the use of compounds as 5-HT$_4$ receptor antagonists in the treatment of gastrointestinal disorders, CNS disorders and/or cardiovascular disorders, and to certain novel compounds having 5-HT$_4$ receptor antagonist activity.

European Journal of Pharmacology 146 (1988), 187–188, and Naunyn-Schmiedeberg's Arch. Pharmacol. (1989) 340: 403–410, describe a non classical 5-hydroxytryptamine receptor, now designated the 5-HT$_4$ receptor, and that ICS 205-930, which is also a 5-HT$_3$ receptor antagonist, antagonises at this receptor.

Some 5-HT$_3$ receptor antagonists have been disclosed as of potential use in the treatment of certain aspects of irritable bowel syndrome (see EP-A-189002 (Sandoz Limited) and EP-A-201165 (Beecham Group p.l.c)).

5-HT$_3$ receptor interactions which are of potential use in the treatment of IBS are those associated either with the visceral pain and abnormal perception of sensation aspects of this disease, or they are related to the ability of some 5-HT$_3$ receptor antagonists to cause constipation in volunteers.

Some 5-HT$_3$ receptor antagonists have been disclosed as of potential use in the treatment of gastrointestinal disorders associated with upper gut motility [see EP-A-226266 (Glaxo Group Ltd.) and EP-A-189002 (Sandoz Limited)]. 5-HT$_3$ receptor antagonists are also well known antiemetics, such as ondansetron, granisetron and tropisetron (see Drugs of the Future 1989, 14 (9) p.875—F. D. King and G. J. Sanger).

PCT/GB91/00650 (SmithKline and French Laboratories Limited) describes the use of cardiac 5-HT$_4$ receptor antagonists in the treatment of atrial arrhythmias and stroke.

EP-A-36269 (Beecham Group p.l.c.) describes a group of compounds of potential use in the treatment of gastrointestinal motility disorders.

WO 92/10494 (Beecham Group p.l.c.) describes 5-HT$_3$ receptor antagonists derived from a benzoic acid nucleus 2,3 disubstituted by alkylenedioxy.

It has now been discovered that certain of the compounds embraced by the general formulae disclosed therein, and related compounds, have 5-HT$_4$ receptor antagonist properties, and are therefore of potential use in the treatment of IBS or atrial arrhythmias and stroke.

The compounds of the present invention also have a potential use in the treatment of CNS disorders such as anxiety and/or migraine, in the treatment of upper gut motility disorders and as antiemetics.

When used herein, 'treatment' includes prophylaxis as appropriate.

Accordingly, the present invention provides the use of a compound of formula (I) or a pharmaceutically acceptable salt thereof:

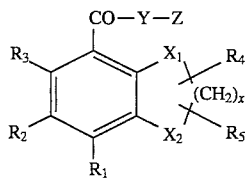

in which $X_1$—$(CH_2)_x$—$X_2$ forms a 5–7 membered ring wherein:

$X_1$ is O or S;

$X_2$ is O, S, NR or NRCO wherein R is hydrogen or $C_{1-6}$ alkyl;

x is 1, 2 or 3;

$R_1$ is hydrogen, amino, halo, $C_{1-6}$ alkyl, hydroxy or $C_{1-6}$ alkoxy;

$R_2$ is hydrogen, halo, $C_{1-6}$ alkyl, $C_{1-6}$ alkoxy, nitro, amino or $C_{1-6}$ alkylthio;

$R_3$ is hydrogen, halo, $C_{1-6}$ alkyl, $C_{1-6}$ alkoxy or amino;

$R_4$ and $R_5$ are independently hydrogen or $C_{1-6}$ alkyl;

Y is O or NH;

Z is of sub-formula (a), (b) or (c):

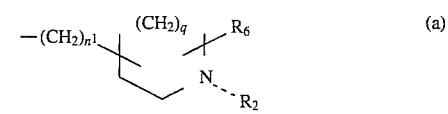

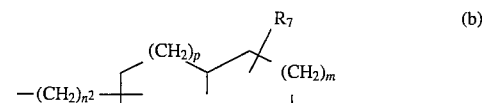

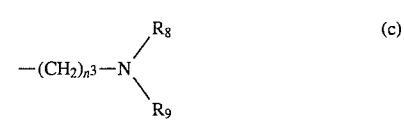

wherein

—$(CH_2)_n{}^1$ is attached at carbon or nitrogen and $n^1$ is 1, 2, 3 or 4;

$n^2$ is 1 or 2;

$n^3$ is 2, 3, 4 or 5;

q is 0, 1, 2 or 3;

p is 0, 1 or 2;

m is 0, 1 or 2;

$R_a$ is hydrogen or a lipophilic group, such as $C_{1-12}$ alkyl or aralkyl;

$R_6$, $R_7$ and $R_8$ are independently hydrogen or $C_{1-6}$ alkyl; and $R_9$ is hydrogen or $C_{1-10}$ alkyl;

or a compound of formula (I) wherein the CO—Y linkage is replaced by a heterocyclic bioisostere;

in the manufacture of a medicament for use as a 5-HT$_4$ receptor antagonist.

Examples of alkyl or alkyl containing groups include $C_1$, $C_2$, $C_3$, $C_4$, $C_5$, $C_6$, $C_7$, $C_8$, $C_9$, $C_{10}$, $C_{11}$ or $C_{12}$ branched, straight chained or cyclic alkyl, as appropriate. $C_{1-4}$ alkyl groups include methyl, ethyl n- and iso-propyl, n-, iso-, sec- and tert-butyl. Cyclic alkyl includes cyclopropyl, cyclobutyl, cyclopentyl, cyclohexyl, cycloheptyl and cyclooctyl.

Aryl includes phenyl and naphthyl optionally substituted by one or more substituents selected from halo, $C_{1-6}$ alkyl and $C_{1-6}$ alkoxy, a suitable value for $R_a$ aralkyl, being benzyl.

Halo includes fluoro, chloro, bromo and iodo, preferably chloro.

A suitable bioisostere for the amide or ester linkage containing Y in formula (I), is of formula (d)

wherein the dotted circle represents one or two double bonds in any position in the 5-membered ring;

H, J and I independently represent oxygen, sulphur, nitrogen or carbon, provided that at least one of H, J and I is other than carbon;

U represents nitrogen or carbon.

Suitable examples of (d) are as described for X, Y and Z in EP-A-328200 (Merck Sharp & Dohme Ltd.), such as an oxadiazole moiety.

Suitable examples of the $X_1$—$(CH_2)_x$—$X_2$ moiety include O—$(CH_2)_2$—O, O—$(CH_2)_3$—O, O—$CH_2$—O, O—$(CH_2)_2$—$NR_4$, O—$(CH_2)_2$—S or O—$CH_2$—$CONR_4$, wherein any of the methylene linkages are optionally mono- or di-substituted by $C_{1-6}$ alkyl groups, such as methyl. Preferably $X_1$—$(CH_2)_2$—$X_2$ is O—$(CH_2)_2$—O.

$R_1$ is preferably hydrogen or amino.

$R_2$ is preferably hydrogen or halo.

$R_3$ is preferably hydrogen or halo.

$R_4$ and $R_5$ are often hydrogen. When $R_4$/$R_5$ is $C_{1-6}$ alkyl, it is often methyl. In particular $R_4$ and $R_5$ are methyl such that the disubstituent containing $X_1$ and $X_2$ is O—$C(CH_3)_2$—O.

Y is preferably O.

When Z is of sub-formula (a), $n^1$ is preferably 2, 3 or 4 when the azacycle is attached at the nitrogen atom and $n^1$ is preferably 1 when the azacycle is attached at a carbon atom, such as the 4-position when q is 2.

When Z is of sub-formula (b), $n^2$ is preferably such that the number of carbon atoms between the ester or amide linkage is from 2 to 4 carbon atoms.

Suitable values for p and m include p=m=1; p=0, m=1, p=1, m=2.

When Z is of sub-formula (c), $n^3$ is preferably 2, 3 or 4.

$R_8$ and $R_9$ are preferably both alkyl, especially one of $R_8$ and $R_9$ is $C_4$ or larger alkyl.

Specific values of Z of particular interest are as follows:

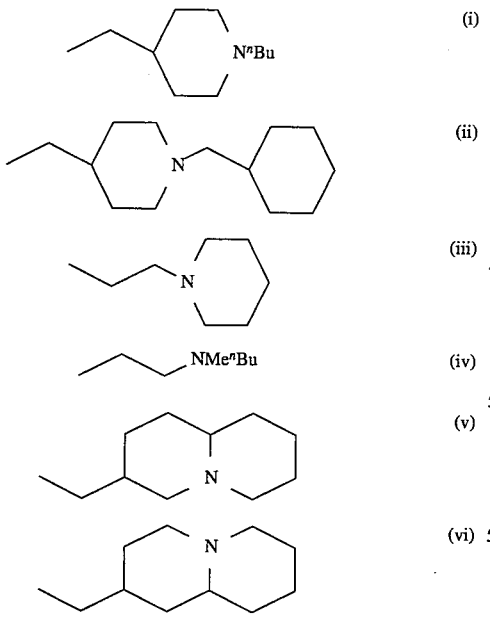

The invention also provides novel compounds of and within formula (I), in particular, with side chains (i), (ii), (iii), (iv), (v) or (vi).

Other values of Z of interest are described with reference to the Examples, in particular, wherein the side chain of formula (i) or (ii) is replaced by a corresponding side chain with an alkyl or optionally substituted benzyl N-substituent and/or wherein the 4-piperidinyl group is replaced by 3-pyrrolidinyl or 3-azetidinyl.

The invention also provides novel compounds within formula (I) having $X_1$—$(CH_2)_x$—$X_2$ as O—$(CH_2)_2$—O, in particular those wherein the side chain Z is of sub-formula (a) or (c).

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

Examples of pharmaceutically acceptable salts include quaternary derivatives of the compounds of formula (I) such as the compounds quaternised by compounds $R_x$-T wherein $R_x$ is $C_{1-6}$ alkyl, phenyl-$C_{1-6}$ alkyl or $C_{5-7}$ cycloalkyl, and T is a radical corresponding to an anion of an acid. Suitable examples of $R_x$ include methyl, ethyl and n- and iso-propyl; and benzyl and phenethyl. Suitable examples of t include halide such as chloride, bromide and iodide.

Examples of pharmaceutically acceptable salts also include internal salts such as N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

It will also be realised that the $(CH_2)_n2$ moiety in compounds of formula (I) wherein Z is (b), may adopt an α or β or configuration with respect to the fused azabicyclic moiety.

The compounds of formula (I) wherein CO—Y is an ester or amide linkage are prepared by conventional coupling of the Z moiety with the appropriate acid. Suitable methods are as described in GB 2125398A (Sandoz Limited), GB 1593146A, EP-A-36269, EP-A-289170 and WO 92/05174 (Beecham Group p.l.c.). When CO—Y is replaced by a heterocyclic bioisostere, suitable methods are described in EP-A-328200 (Merck Sharp & Dohme Limited).

The invention also comprises a process for preparing the novel compounds of formula (I) which comprises reacting an appropriate benzoic acid derivative with an appropriate alcohol or amine. A process comprises reacting a benzoic acid derivative wherein the aromatic substituents are as required in the end compound of formula (I), or substituents convertible thereto, with an alcohol or amine containing Z or a group convertible thereto, and thereafter if necessary, converting the benzoic acid substituents and/or Z, and optionally forming a pharmaceutically acceptable salt.

Suitable examples of conversions in the aromatic substituents include chlorination of hydrogen to chloro, reduction of nitro to amino, dehydrohalogenation such as debromination, and/or elaboration of a 2,3-disubstituted benzoic acid with ethylene glycol to form the benzodioxan.

Suitable examples of conversions in the Z containing moiety include conventional modifications of the N-substituent by substitution and/or deprotection or, in the case of a 2-, 3- or 4- substituted piperidyl desired end compound, reduction of an appropriate pyridyl derivative.

Any elaboration of X and/or Z is, however, usually carried out prior to ester or amide coupling.

Azabicyclic side chain $(CH_2)_n2$—OH intermediates when Z is (b) in formula (I), are known compounds or may be prepared from the ketones of formula (II):

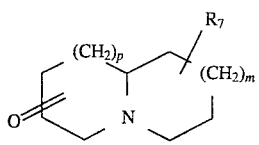

according to conventional methods.

The compounds of the present invention are 5-HT$_4$ receptor antagonists and it is thus believed may generally be used in the treatment or prophylaxis of gastrointestinal disorders, cardiovascular disorders and CNS disorders.

They are of potential interest in the treatment of irritable bowel syndrome (IBS), in particular the diarrhoea aspects of IBS, i.e., these compounds block the ability of 5-HT to stimulate gut motility via activation of enteric neurones. In animal models of IBS, this can be conveniently measured as a reduction of the rate of defaecation. They are also of potential use in the treatment of urinary incontinence which is often associated with IBS.

They may also be of potential use in other gastrointestinal disorders, such as those associated with upper gut motility, and as antiemetics. In particular, they are of potential use in the treatment of the nausea and gastric symptoms of gastro-oesophageal reflux disease and dyspepsia. Antiemetic activity is determined in known animal models of cytotoxic-agent/radiation induced emesis.

Specific cardiac 5-HT$_4$ receptor antagonists which prevent atrial fibrillation and other atrial arrhythmias associated with 5-HT, would also be expected to reduce occurrence of stroke (see A. J. Kaumann 1990, Naunyn-Schmiedeberg's Arch. Pharmacol. 342, 619–622, for appropriate animal test method).

Anxiolytic activity is likely to be effected via the hippocampus (Dumuis et al 1988, Mol Pharmacol., 34, 880–887). Activity can be demonstrated in standard animal models, the social interaction test and the X-maze test. Migraine sufferers often undergo situations of anxiety and emotional stress that precede the appearance of headache (Sachs, 1985, Migraine, Pan Books, London). It has also been observed that during and within 48 hours of a migraine attack, cyclic AMP levels are considerably increased in the cerebrospinal fluid (Welch et al., 1976, Headache 16, 160–167). It is believed that a migraine, including the prodomal phase and the associated increased levels of cyclic AMP are related to stimulation of 5-HT$_4$ receptors, and hence that administration of a 5-HT$_4$ antagonist is of potential benefit in relieving a migraine attack.

The invention also provides a pharmaceutical composition comprising a compound of formula (I), or a pharmaceutically acceptable salt thereof, and a pharmaceutically acceptable carrier.

Such compositions are prepared by admixture and are usually adapted for enteral such as oral, nasal or rectal, or parenteral administration, and as such may be in the form of tablets, capsules, oral liquid preparations, powders, granules, lozenges, reconstitutable powders, nasal sprays, suppositories, injectable and infusable solutions or suspensions. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of irritable bowel syndrome, dyspepsia, atrial arrhythmias and stroke, anxiety and/or migraine in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.05 to 1000 mg for example 0.5 to 500 mg, of the compound of the invention. Unit doses may be administered once or more than once a day, for example, 2, 3 or 4 times a day, more usually 1 to 3 times a day, that is in the range of approximately 0.0001 to 50 mg/kg/day, more usually 0.0002 to 25 mg/kg/day.

No adverse toxicological effects are indicated within the aforementioned dosage ranges.

The invention also provides a compound of formula (I) or a pharmaceutically acceptable salt thereof for use as an active therapeutic substance, in particular for use in the treatment of irritable bowel syndrome, gastro-oesophageal reflux disease, dyspepsia, atrial arrhythmias and stroke, anxiety and/or migraine.

The following Examples illustrate the preparation of compounds of formula (I); the following descriptions relate to intermediates (Descriptions 1–3 and 11 are nuclei incorporating intermediates containing $X_1$—$(CH_2)_x$—$X_2$, Descriptions 4–9 and 10 are side chain Z containing intermediates and Descriptions 12 onwards are piperidyl intermediates prepared from the corresponding compound wherein Z is of sub-formula (a), prepared from the corresponding pyridyl derivative.

EXAMPLES

| | $R_1$ | $R_2$ | $R_3$ | $X_1/X_2$ | Y | Z |
|---|---|---|---|---|---|---|
| E1 | $NH_2$ | Cl | H | O—$(CH_2)_2$—O | O | (i) |
| E2 | $NH_2$ | H | H | O—$(CH_2)_2$—O | O | (i) |
| E3 | H | Br | H | O—$(CH_2)_2$—O | O | (i) |
| E4 | H | H | H | O—$(CH_2)_2$—O | O | (i) |
| E5 | H | Cl | H | O—$(CH_2)_2$—O | O | (i) |
| E6 | $NH_2$ | Cl | Cl | O—$(CH_2)_2$—O | O | (i) |
| E7 | $NH_2$ | I | H | O—$(CH_2)_2$—O | O | (ii) |
| E8 | $NH_2$ | Cl | H | O—$(CH_2)_2$—O | O | (v) ax |
| E9 | $NH_2$ | Cl | H | O—$(CH_2)_2$—O | O | (v) eq |
| E10 | $NH_2$ | Cl | H | O—$(CH_2)_2$—O | O | (ii) |
| E11 | H | Cl | H | O—$(CH_2)_2$—O | O | (vi) eq |
| E12 | $NH_2$ | Cl | H | O—$(CH_2)_2$—O | O | (vi) eq |
| E13 | $NH_2$ | Cl | H | O—$(CH_2)_2$—O | NH | epm |
| E14 | $NH_2$ | Cl | H | O—$(CH_2)_2$—O | NH | (i) |
| E15 | $NH_2$ | Cl | H | O—$(CH_2)_2$—O | NH | (ii) |
| E16 | $NH_2$ | Cl | H | O—$(CH_2)_2$—O | O | pm |
| E17 | H | H | H | O—$(CH_2)_2$—O | ox | pp |
| E18 | H | H | H | O—$CH_2$—O | O | (i) |
| E19 | H | Cl | H | O—$CH_2CONH$ | O | (i) |
| E20 | H | Cl | H | O—$CH_2CONCH_3$ | O | (i) |
| E21 | H | Cl | H | O—$(CH_2)_2NH$ | O | (i) |

| | $R_1$ | $R_2$ | $R_3$ | Z |
|---|---|---|---|---|
| $X_1/X_2$ = O—$(CH_2)_2$—O; Y = O | | | | |
| E22 | $NH_2$ | Cl | H | 1-methyl-4-piperidylmethyl |
| E23 | $NH_2$ | Cl | H | 1-ethyl-4-piperidylmethyl |
| E24 | $NH_2$ | Cl | H | 1-propyl-4-piperidylmethyl |
| E25 | $NH_2$ | Cl | H | 1-$^i$butyl-4-piperidylmethyl |
| E26 | $NH_2$ | Cl | H | 1-cyclopropylmethyl-4-piperidylmethyl |
| E27 | $NH_2$ | Cl | H | 1-pentyl-4-piperidylmethyl |
| E28 | $NH_2$ | Cl | H | 2-methylbutyl-4-piperidylmethyl |
| E29 | $NH_2$ | Cl | H | 2-methoxyethyl-4-piperidylmethyl |
| E30 | $NH_2$ | Cl | H | 1-benzyl-4-piperidylmethyl |
| E31 | $NH_2$ | Cl | H | 2-cyclohexylethyl-4-piperidylmethyl |
| E32 | $NH_2$ | Cl | H | 1-hexyl-4-piperidylmethyl |
| E33 | $NH_2$ | Cl | H | 1-heptyl-4-piperidylmethyl |
| E34 | $NH_2$ | Cl | H | 1-octyl-4-piperidylmethyl |
| E35 | $NH_2$ | Cl | H | 1-nonyl-4-piperidylmethyl |
| E36 | $NH_2$ | Cl | H | 1-decyl-4-piperidylmethyl |
| E37 | $NH_2$ | Cl | H | 1-undecyl-4-piperidylmethyl |
| E38 | $NH_2$ | Cl | H | 1-dodecyl-4-piperidylmethyl |
| E39 | $NH_2$ | Cl | H | 1-(4-fluorobenzyl)-4-piperidylmethyl |
| E40 | $NH_2$ | Cl | H | 1-(4-methoxybenzyl)-4-piperidylmethyl |
| E41 | $NH_2$ | Cl | H | 1-(4-methylbenzyl)-4-piperidylmethyl |
| E42 | $NH_2$ | Cl | H | 1-phenylethyl-4-piperidylmethyl |
| $[X_1/X_2$ = O—$(CH_2)_2$—O; Y = NH] | | | | |
| E43 | $NH_2$ | Cl | H | 1-pentyl-4-piperidylmethyl |
| E44 | $NH_2$ | Cl | H | 1-cyclohexylethyl-4-piperidylmethyl |
| E45 | $NH_2$ | Cl | H | 1-isobutyl-4-piperidylmethyl |
| E46 | $NH_2$ | Cl | H | 1-(2-methylbutyl)-4-piperidylmethyl |
| E47 | $NH_2$ | Cl | H | 4-piperidylmethyl |
| E48 | $NH_2$ | Cl | H | 1-methyl-4-piperidylmethyl |
| E49 | $NH_2$ | Cl | H | 1-propyl-4-piperidylmethyl |
| E50 | $NH_2$ | Cl | H | 1-benzyl-4-piperidylmethyl |
| E51 | $NH_2$ | Cl | H | 1-butyl-1-methyl-4-piperidylmethyl iodide |
| E52 | $NH_2$ | I | H | 1-butyl-4-piperidylmethyl |
| E53 | Cl | H | H | 1-butyl-4-piperidylmethyl |
| E54 | H | Br | Br | 1-butyl-4-piperidylmethyl | epm = 1-ethyl-4-piperidyl
pm = 4-piperidylmethyl
ox = where CO—Y replaced by 1,2,4-oxadiazole
pp = 3-(piperidino)propyl

Example 1

8-Amino-7-chloro-(1-butyl-4-piperidyl)methyl-1,4-benzodioxan-5-carboxylate (E1)

A suspension of 8-amino-7-chloro-1,4-benzodioxan-5-carboxylic acid (prepared from the corresponding 7-H acid[1] by chlorination of the protected form) (720 mg) was dissolved in acetonitrile (10 ml). Bis carbonyldiimidazole (500 mg) was added and the reaction mixture stirred for 2 hours. The solvent was removed in vacuo and the residue dried. A solution of 1-butyl-4-piperidinemethanol (510 mg) in dry THF (20 ml) was added dropwise to a solution of $^n$butyl-lithium (1.88 ml of a 1.6M solution in hexane) at 0° C. and the solution was stirred for 15 minutes. The imidazolide from above was redissolved in dry THF (25 ml) and the solution added dropwise to the solution of the lithium alkoxide in dry THF. The reaction mixture was stirred at room temperature overnight. After removal of solvent the residue was partitioned between EtOAc and $H_2O$ and the EtOAc layer separated. This solution was washed several times with water and dried ($MgSO_4$). Evaporation of solvent gave a yellow gum that was purified by column chromatography on $SiO_2$ using $CHCl_3$, 95%, MeOH, 5% as eluant. The product was isolated as the hydrochloride salt, mp 243°–4° C.

$^1$H NMR 250 MHz (CDCl$_3$) (free base) δ: 7.49 (s,1H), 4.48 (bs,2H), 4.26–4.38 (m,4H), 4.08 (d,2H), 2.93–3.05 (bd,2H), 2.30–2.40 (m,2H), 1.20–2.05 (m,11H), 0.90 (t,3H).

Examples 2 to 12

The following compounds were prepared analogously:
8-Amino-(1-butyl-4-piperidyl)methyl-1,4-benzodioxan-5-carboxylate (E2)

$^1$H NMR 250 MHz (CDCl$_3$) (free base) δ: 7.39(d,1H) 6.24(d,1H) 4.3–4.42(m,4H) 4.05–4.16(4H) 2.9–3.1(bd, 2H)2.3–2.4(m, 2H) 1.2–2.05(m, 11H) 0.90(t,3H)

7-Bromo-5-(1-butyl-4-piperidyl)methyl-1,4-benzodioxan-5-carboxylate (E3)

mp 205°–6° C. (hydrochloride salt)

$^1$H NMR 250 MHz (CDCl$_3$) (free base) δ: 7.5(d, 1H)7.12(d,1H), 4.3–4.42(m,4H) 4.12(d,2H) 2.9–3.05(bd, 2H) 2.3–2.4(m, 2H) 1.22–2.05(m,11H) 0.92(t,3H)

(1-Butyl-4-piperidyl)methyl-1,4-benzodioxan-5-carboxylate (E4)

mp 144°–6° C. (hydrochloride salt)

¹H NMR 250 MHz (CDCl₃)(free base) δ: 7.38(dd, 1H) 7.0(dd, 1H) 6.82(t,1H) 4.28–4.4(m,4H) 4.12(d,2H) 2.9–3.05(bd,2H) 2.3–2.4(m,2H) 1.22–2.05(m,11H) 0.92(t, 3H)

7-Chloro-(1-butyl-4-piperidyl)methyl-1,4-benzodioxan-5-carboxylate (E5)

mp 185°–6° C. (hydrochloride salt)

¹H NMR 250 MHz (CDCl₃) (free base) δ: 7.37(d,1H), 7.02(d,1H),4.25–4.40(m,4H), 4.14(d,2H), 2.98(bd,2H), 2.28–2.38(m,2H), 1.24–2.00(m,11H), 0.92(t,3H)

8-Amino-6,7-dichloro-(1-butyl-4-piperidyl)methyl, 1,4-benzodioxan-5-carboxylate (E6)

mp 168°–9° C. (hydrochloride salt)

¹H NMR 250 MHz (CDCl₃) δ: 4.39(s,2H), 4.28–4.37(m,4H), 4.15(d,2H), 2.9–3.05(bd,2H), 2.3–2.4(m, 2H), 1.22–1.98(m, 11H),0.92(t,3H)

8-Amino-7-iodo-(1-cyclohexylmethyl-4-piperidyl)methyl-1,4-benzodioxan-5-carboxylate (E7)

¹H NMR 250 MHz (CDCl₃) (free base) δ: 7.79(s,1H), 4.50–4.59(d,2H), 4.28–4.37(m,4H), 4.15(d,2H), 2.90–3.06 (bd,2H), 0.80–2.30(m,20H)

8-Amino-7-chloro-1,4-benzodioxan-(αx-3-quinolizidinyl) methyl carboxylate (E8)

mp 139°–40° C.

¹H NMR 250 MHz (CDCl₃) (free base) δ: 7.42 (s,1H), 4.19–4.5 (m,8H) 2.72(dd,1H), 2.60(bd,1H), 1.10–2.11(m, 14H)

8-Amino-7-chloro-1,4-benzodioxan-(eq-3-quinolizidinyl) methyl carboxylate (E9)

¹H NMR 250 MHz (CDCl₃) (free base) δ: 7.49(s,1H), 4.48(bs,2H), 4.28–4.38(m,4H),3.95–4.15(m,2H), 3.0(bd, 1H), 2.83(bd,1H), 1.01–2.20(m,14H)

8-Amino-7-chloro-(1-cyclohexylmethyl-4-piperidyl)methyl-1,4-benzodioxan-5-carboxylate (E10)

mp 185°–6° C. (hydrochloride salt)

¹H NMR 250 MHz (CDCl₃) (free base) δ: 7.49(s,1H), 4.48(bs,2H), 4.30–4.38(m,4H),4.08(d,2H), 2.82–2.91(bd, 2H), 2.10(d,2H), 0.80–1.95(m,18H)

eq-Quinolizidin-2-ylmethyl-7-chloro-1,4-benzodioxan-5-carboxylate (E11)

mp 191°–192° C. (hydrochloride salt)

1H NMR (d⁶ DMSO) (HCl salt) δ: 7.24(d,1H), 7.20(d, 1H), 4.28–4.36(m,4H), 4.11(d,2H), 3.25–3.36(m,2H), 2.76–3.11(m,1H), 2.01–2.13(m,1H), 1.36–1.92(m,10H)

eq-Quinolizidin-2-ylmethyl-8-amino-7-chloro-1,4-benzodioxan-5-carboxylate (E12)

mp 173°–175° C.

¹H NMR 250 MHz (CDCl₃) (free base) δ: 7.48(s,1H), 4.45(brs,2H), 4.28–4.40(m,4H), 4.07(d,2H), 2.76–2.94(m, 2H), 1.00–2.15(m,14H)

Example 13

8-Amino-7-chloro-(1-ethyl-4-piperidyl)methyl-1,4-benzodioxan-5-carboxamide (E13)

A solution of 8-amino-7-chloro-1,4-benzodioxan-5-carboxylic acid (see Example 1) (500 mg, 0.0022 mole) in acetonitrile (30 ml) was treated with biscarbonyl diimidazole (356 mg, 0.0022 mole). The mixture was stirred at room temperature for 2 hours.

A solution of 1-ethyl-4-aminomethylpiperidine (312 mg, 0.0022 mole) in acetonitrile (25 ml) was added and the reaction mixture was stirred at room temperature overnight. The solvent was removed in vacuo and the residue partitioned between EtOAc and H₂O. The EtOAc layer was removed, washed several times with H₂O, dried (MgSO₄) and concentrated to give an orange gum that was purified by column chromatography on SiO₂ using chloroform with increasing proportions of methanol as eluant. The product was isolated as a pale gum.

¹H NMR 250 MHz (CDCl₃) (free base) δ: 7.69(s,1H), 7.50(bt, 1H), 4.29–4.39(m, 6H), 3.25(t,2H), 2.94(bd,2H), 2.38(dd,2H) 1.20–1.95(m,7H), 1.01(t,3H)

Examples 14 and 15

The following compounds were prepared by the method described for Example 13.

8-Amino-7-chloro-(1-butyl -4-piperidyl)methyl-1,4-benzodioxan-5-carboxamide (E14)

mp 75°–6° C.

¹H NMR 250 MHz (CDCl₃) (free base) δ: 7.73(s,1H), 7.58(bt, 1H), 4.30–4.45(m.6H), 3.30(t,2H), 3.0–3.1(bd,2H), 2.39–2.48(m,2H), 2.0–2.14(bt, 2H), 1.20–1.82(m,9H), 0.92(t,3H)

8-Amino-7-chloro-(1-cyclohexylmethyl-4-piperidyl)methyl-1,4-benzodioxan-5-carboxamide (E15)

¹H NMR 250 MHz (CDCl₃) (free base) δ: 7.72(s,1H), 7.55(bt, 1H), 4.30–4.41(m,6H), 3.3(t,2H), 2.82–2.95(bd, 2H), 2.10(d,2H), 0.78–1.9(m,18H)

Example 16

8-Amino-7-chloro-(4-piperidylmethyl )-1,4-benzodioxan-5-carboxylate hydrochloride (E16)

a) To a stirred solution of 8-amino-7-chloro-1,4-benzodioxan-5-carboxylic acid¹ (1.10 g) in acetonitrile was added bis-carbonyldiimidazole (0.77 g). The reaction mixture was stirred at room temperature for 1.5 hours. The solvent was removed under reduced pressure to afford crude 8-amino-7-chloro-1,4-benzodioxan-5-imidazolide.

b) To a solution of N-tert-butoxycarbonyl-4-hydroxymethyl piperidine (0.25 g) in dry THF (10 ml) was added methyllithium (1.5M in diethylether; 0.78 ml) at 0° C. under a nitrogen atmosphere. Stirring was continued at ambient temperature for 10 min. 8-Amino-7-chloro-1,4-benzodioxan-5-imidazolide (0.33 g) in THF (10 ml) was added to the reaction mixture and stirring continued for 2 hours. The reaction mixture was cooled to 0° C. and water was added. The solvent was removed under reduced pressure and the residue partitioned between chloroform and water. The organic phase was washed with water (3×), dried (Na₂SO₄) filtered and concentrated in vacuo. Flash chromatography on silica using chloroform and ethanol as eluant gave the title compound (0.26 g).

¹H NMR 250 MHz (CDCl₃) δ: 7.47(s,1H), 4.49(s,2H), 4.08–4.22(m,4H), 2.64–2.80(m,2H), 1.84–2.01(m, 1H), 1.70–1.83(m,2H), 1.46(s,9H), 1.18–1.38(m,2H)

c) HCl(g) was bubbled into a cooled solution of 8-amino-7-chloro-(N-tert-butoxycarbonyl-4-piperidylmethyl)-1,4-benzodioxan-5-carboxylate (0.26 g) in dioxan (50 ml) for 25 min. The solvent was concentrated in vacuo and the residue triturated with Et₂O to afford pure title compound (0.12 g).

mp 249°–251° C.

¹H NMR 250 MHz (DMSO) δ: 8.99–9.10(m,1H), 8.59–8.78(m,1H), 7.29(s,1H), 5.73(s,2H), 4.25–4.34(s,4H), 4.03(d,2H), 3.20–3.42(m,2H), 2.75–2.97(m,2H), 1.76–2.06(m,3H), 1.48–1.57(m,2H)

Example 17

5[3-(Piperidino)propyl]-3-[benzo-1,4-dioxan-5-yl]-1,2,4-oxadiazole (E17)

1,4-Benzodioxan-5-carboxamide oxime (D3) (0.300 g 1.55 mmol) was dissolved in dry THF (10 ml) with stirring, and treated with ground 4A molecular sieves (1 g), under nitrogen. After 30 minutes, sodium hydride (80% dispersion in mineral oil) (0.051 g, 1.71 mmol) was added. The mixture was then heated to reflux. After 30 minutes, the mixture was allowed to cool for a short period and ethyl-4-(piperidino) butyrate (0.340 g, 1.71 mmol) was added. The reaction mixture was then heated to reflux for a further 2.5 h, before being allowed to cool. The reaction mixture was then filtered. The filter pad was then washed with THF (2×). The flitrate was evaporated under reduced pressure. The residue was purified by silica-gel chromatography, eluting with pentane: EtOAc 1:1–>2:3 to give the title compound as a pale yellow oil, which was converted to the hydrochloride salt mp 175°–176° C.

$^1$H NMR 250 MHz (CDCl$_3$) δ: 12.20–12.5(s br, 1H), 7.52(dd, 1H),, 6.90–7.08 (m,2H), 4.45(m,2H), 4.35(m,2H), 3.5–3.7(m,2H), 2.97–3.20(m,4H), 2.47–2.80(m,4H), 2.15–2.45(m,2H), 1.74–2.00(m,3H), 1.30–1.54(m, 1H)

Example 18

(1-Butyl-4-piperidyl)methyl-1,3-benzodioxole-4-carboxylate hydrochloride (E18)

Following the procedure outlined in Example 1 1,3-benzodioxole-4-carboxylic acid (D11) (705 mg) was converted to the title compound (393 mg, 29%) mp 168–9° C.

$^1$H NMR 250 MHz (CDCl$_3$) δ: 7.4 (d, 1H), 6.98 (d, 1H), 6.86 (t, 1H), 6.10 (s, 2H), 4.20 (d, 2H), 3.04 (br d, 2H), 2.45–2.3 (m, 2H), 2.1–1.2 (m, 11H), 0.94 (t, 3H).

Examples 19 to 21

The parent acids for Examples 19–21 are described in EP-A-407137 and 313393 (Yoshitomi).
(1-Butyl-4-piperidyl)methyl-6-chloro-3,4-dihydro-3-oxo-2H-1,4-benzoxazine-8-carboxylate (E19)
mp 245°–247° C. (HCl salt)

$^1$H NMR 250 MHz, (CD$_3$SOCD$_3$) (HCl salt) δ: 11.17 (s, 1H), 10.34–10.10 (s, 1H), 7.41 (d, 1H), 7.21 (d, 1H), 4.80 (s, 2H), 4.22 (d, 2H), 3.57 (m, 2H), 3.20–2.85 (m, 4H), 2.12–1.95 (m, 3H), 1.90–1.60 (m, 4H), 1.40 (m, 2H), 1.00 (t, 3H)

(1-Butyl-4-piperidyl)methyl-6-chloro-4-methyl-3,4-dihydro-3-oxo-2H-1,4-benzoxazine-8-carboxylate (E20)
mp 87°–88° C.

$^1$H NMR 250 MHz, (CDCl$_3$) δ: 7.49 (d, 1H), 7.10 (d, 1H), 4.18 (d, 2H), 3.38 (s, 3H), 3.00 (d, 2H), 2.33 (t, 2H), 1.97 (t, 2H), 1.78 (m, 3H), 1.54–1.25 (m, 6H), 0.92 (t, 3H)

(1-Butyl-4-piperidyl)methyl-6-chloro-3,4-dihydro-2H-1,4-benzoxazine-8-carboxylate (E21)
mp 177°–178° C. (HCl salt)

$^1$H NMR 250 MHz, (CD$_3$SOCD$_3$) (HCl salt) δ: 10.28 (s, 1H), 6.85 (m, 2H), 6.58 (s, 1H), 4.23 (t, 2H), 4.15 (d, 1H), 3.67 (d, 2H), 3.45 (m, 3H), 3.10–2.90 (m, 3H), 2.15–1.92 (m, 3H), 1.88–1.60 (m, 4H), 1.40 (m, 2H), 1.00 (t, 3H)

Example 22

8-Amino-7-chloro-5-(1-methyl-4-piperidinylmethyl)-1,4-benzodioxan carboxylate hydrochloride (E22)

To a solution of 8-amino-7-chloro-5-(1H-4-piperidylmethyl)-1,4-benzodioxan carboxylate (E15) (100 mg) and triethylamine (70 µl) in acetone (15 ml) was added iodomethane (20 µl). The reaction mixture was stirred at ambient temperature for 64 h. The solvent was concentrated under reduced pressure and the residue partitioned between chloroform and water. The organic phase was dried (Na$_2$SO$_4$), filtered and concentrated in vacuo. Chromatography on silica using chloroform and ethanol as the eluant gave pure product. Treatment with ethereal HCl afforded the title compound (40 mg).

$^1$H NMR 250 MHz (CDCl$_3$) (free base) δ: 7.49 (s, 1H), 4.53 (bs, 2H), 4.31–4.44 (m, 4H), 4.19 (d, 2H), 3.49 (d, 2H), 2.69–2.85 (m, 5H), 1.97–2.15 (m, 5H)

Examples 23 to 43

Following the procedure outlined in Example 22, from the compound of Example 16, the following compounds were obtained:
8-Amino-7-chloro-5-(1-ethyl-4-piperidyl)methyl-1,4-benzodioxan carboxylate hydrochloride (E23)

$^1$H NMR 250 MHz (CDCl$_3$) (free base) δ: 7.47 (s, 1H), 4.53 (bs, 2H), 4.29–4.46 (m, 4H), 4.17 (d, 2H), 3.44 (d, 2H), 2.95 (q, 2H), 2.51–2.69 (m, 2H), 1.90–2.12 (m, 5H), 1.40 (t, 3H)

8-Amino-7-chloro-5(1-propyl-4-piperidyl)methyl-1,4-benzodioxan carboxylate hydrochloride (E24)

$^1$H NMR 250 MHz (CD$_3$OD) δ: 7.44 (s, 1H), 4.27–4.38 (m, 4H), 4.16 (d, 2H), 3.64 (d, 2H), 2.94–3.13 (m, 4H), 2.03–2.17 (m, 3H), 1.59–1.88 (m, 4H), 1.03 (t, 3H)

8-Amino-7-chloro-5-(1-isobutyl-4-piperidyl)methyl-1,4-benzodioxan carboxylate hydrochloride (E25)

$^1$H NMR 250 MHz (CDCl$_3$) (free base) δ: 7.50 (s, 1H), 4.48 (bs, 2H), 4.31–4.39 (m, 4H), 4.09 (d, 2H), 2.89 (d, 2H), 2.08 (d, 2H), 1.69–1.95 (m, 6H), 1.31–1.49 (m, 2H), 0.91 (d, 6H)

8-Amino-7-chloro-5-(1-cyclopropylmethyl-4-piperidyl)methyl-1,4-benzodioxan carboxylate hydrochloride (E26)

$^1$H NMR 250 MHz (CDCl$_3$) (free base) δ: 7.49 (s, 1H), 4.52 (bs, 2H), 4.29–4.45 (m, 4H), 4.14 (d, 2H), 3.39 (d, 2H), 2.58 (d, 2H), 2.29–2.48 (m, 2H), 1.69–2.00 (m, 5H), 1.04–1.18 (m, 1H), 0.54 (d, 2H), 0.27 (d, 2H)

8-Amino-7-chloro-5-(1-pentyl-4-piperidinyl)methyl-1,4-benzodioxan carboxylate hydrochloride (E27)

$^1$H NMR 250 MHz (CD$_3$OD) δ: 7.43 (s, 1H), 4.31–4.41 (m, 4H), 4.17 (d, 2H), 3.65 (d, 2H), 2.95–3.17 (m, 4H), 2.01–2.18 (m, 3H), 1.61–1.86 (m, 4H), 1.29–1.49 (m, 4H), 0.95 (t, 3H)

8-Amino-7-chloro-5-(2-methylbutyl-4-piperidyl)methyl-1,4-benzodioxan carboxylate hydrochloride (E28)

$^1$H NMR 250 MHz (CD$_3$OD) δ: 7.43 (s, 1H), 4.28–4.43 (m, 4H), 4.18 (d, 2H), 3.65 (d, 2H), 2.95–3.19 (m, 4H), 2.02–2.19 (m, 3H), 1.59–1.78 (m, 5H), 0.97 (d, 6H)

8-Amino-7-chloro-5-(2-methoxyethyl-4-piperidyl)methyl-1,4-benzodioxan carboxylate hydrochloride (E29)

$^1$H NMR 250 MHz (CDCl$_3$) (free base) δ: 7.49 (s, 1H), 4.49 (bs, 2H), 4.30–4.42 (m, 4H), 4.11 (d, 2H), 3.52 (t, 2H), 3.35 (s, 3H), 3.01 (d, 2H), 2.60 (t, 2H), 2.03 (t, 2H), 1.73–1.84 (m, 3H), 1.38–1.57 (m, 2H)

8-Amino-7-chloro-5-(1-benzyl-4-piperidyl)methyl-1,4-benzodioxan carboxylate hydrochloride (E30)

$^1$H NMR 250 MHz (CDCl$_3$) (free base) δ: 7.49 (s, 1H), 7.22–7.40 (m, 5H), 4.49 (bs, 2H), 4.28–4.52 (m, 4H), 4.10 (d, 2H), 3.50 (s, 2H), 2.94 (d, 2H), 2.00 (t, 2H), 1.70–1.85 (m, 3H), 1.33–1.51 (m, 2H)

8-Amino-7-chloro-5-(2-cyclohexylethyl-4-piperidinyl)methyl-1,4-benzodioxan carboxylate hydrochloride (E31)

$^1$H NMR 250 MHz (CDCl$_3$) (free base) δ: 7.49 (s, 1H), 4.47 (bs, 2H), 4.29–4.41 (m, 4H), 4.10 (d, 2H), 3.01 (d, 2H), 2.33–2.44 (m, 2H), 1.99 (t, 2H), 1.35–1.87 (m, 12H), 1.10–1.31 (m, 4H), 0.83–1.01 (m, 2H)

8-Amino-7-chloro-5-(1-hexyl-4-piperidyl)methyl-1,4-benzodioxan carboxylate hydrochloride (E32)

¹H NMR 250 MHz (CDCl₃) (free base) δ: 7.47(s, 1H), 4.48(bs,2H), 4.32–4.42(m,4H), 4.15(d,2H), 3.09–3.24(m, 2H), 2.46–2.59(m,2H), 2.09–2.28(m,2H), 1.79–1.91(m,3H), 1.55–1.73(m,4H), 1.25–1.37(m,6H), 0.84–0.92(m,3H)

8-Amino-7-chloro-5-(1-heptyl-4-piperidyl)methyl 1,4-benzodioxan carboxylate hydrochloride (E33)

¹H NMR 250 MHz (CDCl₃) (free base) δ: 7.48(s,1H), 4.46(bs,2H), 4.30–4.39(m,4H), 4.12(d,2H), 3.11(d,2H), 2.47(t,2H), 2.04(t,2H), 1.79–1.90(m,3H), 1.52–1.69(m,4H), 1.29–1.45(m,8H), 0.83–0.91(m,3H)

8-Amino-7-chloro-5-(1-octyl-4-piperidyl)methyl-1,4-benzodioxan carboxylate hydrochloride (E34)

¹H NMR 250 MHz (CDCl₃) (free base) δ: 7.50(s,1H), 4.46(m,2H), 4.31–4.39(m,4H), 4.12(d, 2H), 3.04–3.13(m, 2H), 2.38–2.48(m,2H), 2.01–2.16(m,2H), 1.77–1.88(m,3H), 1.51–1.65(m,4H), 1.24–1.32(m,10H), 0.85–0.91(m,3H)

8-Amino-7-chloro-5-(1-nonyl-4-piperidyl)methyl-1,4-benzodioxan carboxylate hydrochloride (E35)

¹H NMR 250 MHz (CDCl₃) (free base) δ: 7.47(s,1H), 4.51(bs,2H), 4.31–4.40(m,4H), 4.14(d,2H), 3.22(d,2H), 2.59(t,2H), 2.31(t,2H), 1.62–1.94(m,7H), 1.21–1.35(m, 12H), 0.85–0.93(m,3H)

8-Amino-7-chloro-5-(1-decyl-4-piperidyl)methyl-1,4-benzodioxan carboxylate hydrochloride (E36)

¹H NMR 250 MHz (CDCl₃) (free base) δ: 7.41(s,1H), 4.44(bs,2H), 4.24–4.32(m,4H), 4.08(d,2H), 3.15(d,2H), 2.48–2.57(m,2H), 2.24(d,2H), 1.57–1.88(m,7H), 1.13–1.28(m, 14H), 0.79–0.84(m,3H)

8-Amino-7-chloro-5-(1-undecyl-4-piperidyl)methyl 1-4-benzodioxan carboxylate hydrochloride (E37)

¹H NMR 250 MHz (CDCl₃) (free base) δ: 7.49(s,1H), 4.50(bs, 2H), 4.32–4.41(m,4H), 4.15(d,2I-I), 3.19(d,2H), 2.50–2.58(m,2H), 2.17–2.29(m,2H), 1.80–1.92(m,3H), 1.60–1.78(m,4H), 1.21–1.35(m, 16H), 0.88–0.92(m,3H)

8-Amino-7-chloro-5-(1-dodecyl-4-piperidyl)methyl-1,4-benzodioxan carboxylate hydrochloride (E38)

¹H NMR 250 MHz (CDCl₃) (free base) δ: 7.49(s, 1H), 4.49(bs,2H), 4.33–4.41(m,4H), 4.14(d,2H), 3.18(d,2H), 2.49–2.57(m,3H), 2.22(t,2H), 1.80–1.94(m,3H), 1.57–1.76(m,4H), 1.22–1.33(m,18H), 0.85–0.9 l(m,3H)

8-Amino-7-chloro-5-(1-(4-fluorobenzyl)-4-piperidyl)methyl-1,4-benzodioxan carboxylate hydrochloride (E39)

¹H NMR 250 MHz (CDCl₃) (free base) δ: 7.48(s, 1H), 7.27–7.38(m,2H), 7.01(t,2H), 4.49(bs,2H), 4.30–4.39(m, 4H), 4.11(d,2H), 3.53(s,2H), 2.94(d,2H), 2.04(t,2H), 1.72–1.84(m,3H), 1.39–1.52(m,2H)

8-Amino-7-chloro-5-(1-(4-methoxybenzyl)-4-piperidyl)methyl-1,4-benzodioxan carboxylate hydrochloride (E40)

¹H NMR 250 MHz (CDCl₃) (free base) δ: 7.48(s,1H), 7.22(d,2H), 6.85(d,2H), 4.49(bs,2H), 4.29–4.36(m,4H), 4.09(d,2H), 3.78(s,3H), 3.47(s,2H), 2.91(d,2H), 1.96(t,2H), 1.70–1.80(m,3H), 1.29–1.47 (m,2H)

8-Amino-7-chloro-5-(1-(4-methylbenzyl)-4-piperidyl)methyl-1,4-benzodioxan carboxylate hydrochloride (E41)

¹H NMR 250 MHz (CDCl₃) (free base) δ: 7.48(s,1H), 7.22(d,2H), 7.12(d,2H), 4.45(bs,2H), 4.30–4.38(m,4H), 4.10(d,2H), 3.47(s,2H), 2.92(d,2H), 2.33(s,3H), 2.00(t,2H), 1.70–1.81(m,3H), 1.32–1.50(m,2H).

8-Amino-7-chloro-5-(1-phenethyl-4-piperidyl)methyl-1,4-benzodioxan carboxylate hydrochloride (E42)

¹H NMR 250 MHz (CDCl₃) (free base) δ: 7.50(s,1H), 7.15–7.34(m,5H), 4.49(bs,2H), 4.28–4.41(m,4H), 4.13(d, 2H), 3.07(d,2H), 2.79–2.89(m,2H), 2.55–2.65(m,2H), 2.07(t,2H), 1.71–1.90(m,3H), 1.38–1.54(m,2H)

Example 43

8-Amino-7-chloro-1,4-benzodioxan-5-(1-pentyl-4-piperidyl)methyl carboxamide hydrochloride (E43)

A solution of 8-acetamido-7-chlorobenzodioxan-5-(1-pentyl-4-piperidylmethylcarboxamide) (D13) (60 mg) in ethanol (10 ml) was treated with 10% aqueous NaOH solution (110 μl). The resultant mixture was heated to reflux for 5 h. The solvent was removed in vacuo and the residue partitioned between water and chloroform. The organic phase was dried (Na₂SO₄) filtered and concentrated in vacuo to afford an oil. Treatment with ethereal HCl gave pure title compound (39 mg).

¹H NMR 250 MHz (CDCl₃) (free base) δ: 7.70(s,1H), 7.42–7.53(m, 1H), 4.24–4.49(m,6H), 3.27(t,2H), 2.88(d, 2H), 2.18–2.28(m,2H), 1.84(t,2H), 1.13–1.71(m,11H), 0.83(t,3H)

Examples 44–46

Following the procedure outlined in Example 43 the following compounds were obtained:

8-Amino-7-chloro-1,4-benzodioxan-5-(1-cyclohexylethyl-4-piperidinyl)methyl carboxamide hydrochloride (E44)

¹H NMR 250 MHz (CDCl₃) (free base) δ: 7.69 (s, 1H), 7.42–7.53(m, 1H), 4.22–4.38(m,6H), 3.24(t,2H), 2.85(d, 2H), 2.18–2.31(m,2H), 1.81(t,2H), 0.95–1.72(m,16H), 0.70–0.93(m,2H)

8-Amino-7-chloro-1,4-benzodioxan-5-(1-isobutyl-4-piperidyl)methyl carboxamide hydrochloride (E45)

¹H NMR 250 MHz (CDCl₃) (free base) δ: 7.78(s, 1H), 7.49–7.59(m, 1H), 4.32–4.45(m,6H), 3.34(t,2H), 2.88(d, 2H), 2.07(d,2H), 1.52–1.91(m,6H), 1.23–1.40(m,2H), 0.89(d,6H).

8-Amino-7-chloro-1,4-benzodioxan-5-(1-(2-methylbutyl)-4-piperidyl)methyl carboxamide hydrochloride (E46)

¹H NMR 250 MHz (CDCl₃) (free base) δ: 7.70(s,1H), 7.44–7.53(m,1H), 4.24–4.37(6H), 3.28(t,2H), 2.87(d,2H), 2.19–2.29(m,2H), 1.75–1.90(m,3H), 1.42–1.71(m,4H), 1.15–1.37(m,4H), 0.83(d,6H).

Example 47

8-Amino-7-chloro-1,4-benzodioxan-5-(4-piperidyl)methyl carboxamide hydrochloride (E47)

A solution of 8-acetamido-7-chloro-1,4-benzodioxan-5-(4-piperidyl)methyl carboxamide (D12) (1.65 g) in ethanol (50 ml) was treated with 10% aqueous sodium hydroxide solution (4.5 ml) and the resulting mixture heated to reflux overnight. The solvent was removed in vacuo, the residue saturated with K₂CO₃ and extracted with chloroform. The organic phase was dried (Na₂SO₄) filtered and evaporated under reduced pressure to afford 8-amino-7-chloro-1,4-benzodioxan-5-(4-piperidyl)methylcarboxamide (0.89 g). Treatment with ethereal HCl gave the title compound.

¹H NMR 250 MHz (CDCl₃) (free base) δ: 7.74(s,1H), 6.48–7.54(m,1H), 4.26–4.48(m,6H), 3.32(t,2H), 3.09(d,2H), 2.59(dt,2H), 2.03(bs,1H), 1.62–1.81(m,3H), 1.08–1.28(m, 2H)

Examples 48–50

Following the procedure outlined in Description 13 the following compounds were prepared.

8-Amino-7-chloro-1,4-benzodioxan-5-(1-methyl-4-piperidyl)methyl carboxamide hydrochloride (E48)

¹H NMR 250 MHz (CD₃OD) free base δ: 8.15–8.25(m, 1H), 7.45(s,1H), 4.31–4.48(m,4H), 3.51(d,2H), 3.37–3.41(m,2H), 3.0(t,2H), 2.84(s,3H), 1.88–2.09(m,3H), 1.42–1.63(m,2H)

8-Amino-7-chloro-1,4-benzodioxan-5-(1-ⁿpropyl-4-piperidyl)methyl carboxamide hydrochloride (E49)

$^1$H NMR 250 MHz (CD$_3$OD) (free base) δ: 7.53(s, 1H), 4.38–4.54(m,4H), 3.57(d,2H), 3.27–3.41(m,2H), 2.83–3.15(m,4H), 1.54–2.12(m,7H), 1.03(t,3H)

8-Amino-7-chloro-1,4-benzodioxan-5-(1-benzyl-4-piperidyl)methyl carboxamide hydrochloride (E50)

$^1$H NMR 250 MHz (CDCl$_3$) δ: 7.75(s, 1H), 7.48–7.60(m, 1H), 7.17–7.38(m,5H), 4.28–4.46(m,6H), 3.49(s,2H), 3.31(t,2H), 2.91(d,2H), 1.98(t,2H), 1.52–1.78(m,3H), 1.23–1.42(m,2H). M$^+$ (EI) 359

Example 51

8-Amino-7-chloro-(1-butyl-1-methyl-4-piperidyl)methyl-1,4-benzodioxan-5-carboxylate iodide (E51)

A solution of 8-amino-7-chloro-(1-butyl-4-piperidyl)methyl-1,4-benzodioxan-5-carboxylate hydrochloride (E1) (75 mg) was converted to the free base then dissolved in acetone (10 ml). Iodomethane (20 μml) was added and the mixture was heated under reflux for 3 hours. The solvent was removed in vacuo and the residue dried to give a pale yellow solid (70 mg). The product exists in two isomeric forms.

$^1$H NMR 250 MHz (DMSO) δ: 7.28(s,1H), 5.72(bs.2H), 4.28(bs,4H), 4.08(d,2H), 3.38–3.5(m,2H), 3.2–3.37(m,4H), 3.00(s,3H), 1.20–2.05(m,9H), 0.92(t,3H).

Example 52

8-Amino-7-iodo-1,4-benzodioxan-5-(1-butyl-4-piperidyl)methyl carboxylate hydrochloride (E52)

The title compound was prepared from 8-amino-7-iodo-1,4-benzodioxan-5-carboxylic acid (D1) by the method described for Example 1.

$^1$H NMR 250 MHz (CDCl$_3$) δ: 7.81(s,1H), 4.53(bs,2H), 4.29–4.40(m,4H), 4.09(d,2H), 2.91–3.08(m,2H), 2.28–2.44(m,2H), 1.89–2.08(m,2H), 1.69–1.88(m,3H), 1.23–1.60(6H), 0.93(t,3H).

Example 53

(1-Butyl-4-piperidyl)methyl-8-chloro-1,4-benzodioxan-5-carboxylate (E53)

The title compound was prepared from 8-chloro-1,4-benzodioxan-5-carboxylic acid$^1$ by the method described for Example 1.

mp 153°–154° C. (hydrochloride salt)

$^1$H NMR 250 MHz (CDCl$_3$) (free base) δ: 7.38(d,1H), 6.96(d,1H), 4.41(s,4H), 4.13(d,2H), 2.98(d,2H), 2.32(t,2H), 1.93(t,2H), 1.84–1.65(m,3H), 1.54–1.20(m,6H), 0.92(t,3H)

Example 54

(1-Butyl-4-piperidyl)methyl-6,7-dibromo-1,4-benzodioxan-5-carboxylate (E54)

The title compound was prepared from 6,7-dibromo-1,4-benzodioxan-5-carboxylic acid$^1$ by the method described for Example 1.

mp 175°–177° C. (hydrochloride salt)

$^1$H NMR 250 MHz (CDCl$_3$) (free base) δ: 7.20(s,1H), 4.30(s,4H), 4.20(d,2H), 3.02(d,2H), 2.38(t,2H), 2.00(t,2H), 1.87–1.65(m,3H), 1.55–1.28(m,6H), 0.94(t,3H)

Descriptions (Preparation of Intermediates)

Description 1 (intermediate for Example 7)
8-Amino-7-iodo-1,4-benzodioxan-5-carboxylic acid A solution of 8-amino-1,4-benzodioxan-5-carboxylic acid$^1$ (500 mg, 0.0025 m) in AcOH (50 ml) was treated with a solution of iodine monochloride (0.423 g, 0.0026) in AcOH (10 ml). The reaction mixture was stirred at room temperature for two days. The solvent was removed in vacuo and the residue treated with H$_2$O. A red solid was obtained which was collected by filtration and washed with water. Yield=0.60 g.

$^1$H NMR (250 MHz) DMSO δ: 7.69(s,1H), 5–5.5(b,1H), 4.3(s,6H)

Description 2 (intermediate for Example 6)
8-Amino-6,7-dichloro-1,4-benzodioxan-5-carboxylic acid 8-Acetamido-1,4-benzodioxan-5-carboxylic acid$^1$ (6.14 g, 0.029 m) was suspended in AcOH (200 ml) and a solution of Cl$_2$ in AcOH (52 ml of a solution of 9.6 g in 100 ml) was added. The reaction mixture was stirred at room temperature overnight. The solvent was removed in vacuo and the residue was triturated with water. The precipitated solid was collected by filtration, washed with water and dried to give 6.20 g product.

$^1$H NMR (250 MHz) DMSO δ: 12.4–12.5(b,1H), 9.3(bs, 1H), 4.35(s,4H), 2.07(s,3H)

Description 3 (intermediate for Example 17)
1,4-Benzodioxan-5-carboxamide oxime

Sodium (0.720 g, 0.031 mol) was dissolved with stirring in methanol (8 ml). A solution of hydroxylamine hydrochloride (2.18 g, o.031 mol) in methanol (40 ml) was then added dropwise. The mixture was then stirred at room temperature for ½ hour. The reaction mixture was then filtered, and the filter pad washed with MeOH. The flitrate was then treated with 1,4-benzodioxan-5-nitrile$^2$ (2.52 g, 0.016 mol). The reaction mixture was then stirred and heated to reflux. After 12 h, the reaction mixture was allowed to cool, and was evaporated under reduced pressure to give a brown oily solid. Recrystallisation of this residue from methanol gave the title compound as cream coloured crystals (2.57 g) mp 146°–148° C.

$^1$H NMR (250 MHz) DMSO δ: 9.42(s,1H), 6.75–6.96(m, 3H), 5.62(s,2H), 4.25(s,4H)

Description 4 (Z is of sub-formula (i), Y=O)
1-Butyl-4-piperidinemethanol

A mixture of ethyl isonipecotate (31.4 g, 0.2 mole), K$_2$CO$_3$ (54 g, 0.4 mole) and $^n$BuBr (27.4 g, 0.2 mole) in EtOH (400 ml) was stirred under reflux for 3 hours. The reaction mixture was allowed to cool, filtered through keiselguhr and the filtrate concentrated to give a pale yellow oil. This was dissolved in dry Et$_2$O (200 ml) and added dropwise to a suspension of LiAlH$_4$ (20 g, 0.26 mole) in dry Et$_2$O. The reaction mixture was stirred at room temperature overnight then cooled in an ice bath. Water (20 ml) was carefully added, followed by 20% aq. NaOH (20 ml), followed by water (60 ml). The mixture was stirred at room temperature for 30 minutes then filtered through keiselguhr. The flitrate was concentrated in vacuo to give a colourless oil (25.0 g).

$^1$NMR 250MHz (CDCl$_3$) δ: 3.48(d,2H), 2.93–2.99(bd, 2H), 1.18–2.4(m,14H), 0.9(t,3H)

Description 5 (Z is of sub-formula (ii), Y=O)
1-Cyclohexylmethyl-4-piperidinemethanol This compound was prepared by the method described in Description 4 from ethyl isonipecotate and cyclohexylmethylbromide.

$^1$H NMR 250 MHz, (CDCl$_3$) δ: 3.48(d,2H), 2.84–2.94(bd, 2H), 0.78–2.4(m,21H inc. d,2H)

Description 6 (Z is of sub-formula (ii), Y=NH$_2$)
4-Aminomethyl-1-cyclohexylmethylpiperidine A solution of isonipecotamide (7 g,0.055 mole) in EtOH (150 ml) was treated with K$_2$CO$_3$ (13.8 g, 0.1 mole) and cyclohexylmethylbromide (12.4 g, 0.07 mole) and the reaction mixture was heated under reflux overnight. The mixture was allowed to cool, the solid removed by filtration through keiselguhr and the flitrate concentrated in vacuo to give a pink solid (7.3 g). This amide was suspended in dry THF (30 ml) and the suspension brought to reflux. $BH_3.Me_2S$ (4.8 ml) was added dropwise over 15 minutes then the mixture was heated under reflux for a further hour. $Me_2S$ was removed from the mixture using a reflux ratio head. Heating was continued overnight and the reaction mixture was then cooled. 5N HCl (6 ml) was added then the mixture was heated under reflux overnight. The solution was cooled, basified with 40% aq. NaOH and extracted with $CHCl_3$. Drying and evaporation of solvent gave a colourless oil.

$^1$H NMR 250 MHz ($CDCl_3$) δ: 2.8–2.91(bd,2H), 2.55(d, 2H), 2.09(d,2H), 0.75–1.9(m,20H)

Description 7 (Z is of sub-formula (i), Y=NH)
4-Aminomethyl-1-butylpiperidine

The title compound was prepared by the method described in Description 6 from isonipecotamide and butyl bromide.

$^1$H NMR 250 MHz ($CDCl_3$) δ: 2.88–3.0(bd,2H), 2.56(d, 2H), 1.18–1.95(m,15H), 0.92(t,3H)

Description 8 (Z is epm, Y=NH)
4-Aminomethyl-1-ethylpiperidine

The title compound was prepared by the method described in Description 6 from isonipecotamide and ethyl iodide.

$^1$H NMR 250 MHz ($CDCl_3$) δ: 2.9–3.0 (bd,2H), 2.56(d, 2H), 2.48(dd,2H), 1.1–1.95(m,9H), 1.05(t,3H)

Description 9 (Z is pm, Y=O)
N-tert-Butoxycarbonyl-4-hydroxymethylpiperidine

To a stirred slurry of $LiAlH_4$ (14.48 g) in $Et_2O$ (200 ml) was added, dropwise, a solution of ethyl isonipecotate (19.3 ml) in $Et_2O$ (100 ml) at 0° C. under a nitrogen atmosphere. Stirring was continued at room temperature overnight. The mixture was cooled and $H_2O$ (14.5 ml), 10% aqueous NaOH (21.8 ml) and $H_2O$ (36.2 ml) were added sequentially. The mixture was stirred at room temperature for 1 h. The precipitate was removed by filtration through keiselguhr and the flitrate concentrated under reduced pressure to afford crude 4-hydroxymethylpiperidine (4.71 g). Di-tert-butyl dicarbonate (9.83 g) was added to a solution of 4-hydroxymethylpiperidine (4.71 g) in 50% aqueous THF. Solid $K_2CO_3$ was added to the reaction mixture to maintain pH 9, and the mixture stirred overnight at room temperature. The solvent was concentrated under reduced pressure and the residue partitioned between $Et_2O$ and $H_2O$. The aqueous phase was extracted with $Et_2O$ and the combined organic phase dried ($Na_2SO_4$) filtered and concentrated in vacuo to afford the title compound as a pale yellow solid (6.12 g).

$^1$H NMR 250 MHz ($CDCl_3$) δ: 4.08–4.2(bd, 2H), 3.45–3.52(bt,2H), 2.6–2.78(m,2H), 1.58–1.9(m,4H), 1.46(s, 9H), 1.03–1.22(m,2H)

Description 10
eq-2-Hydroxymethylquinolizidine
was prepared by the method of N.J. Leonard et al. J. Org. Chem., 1957 22, 1445
eq -3-Hydroxymethylquinolizidine
was prepared by the method of H. Lewis and C. Shoppee J. Chem. Soc., 1956, 313.

Description 11 (intermediate for Example 18)
a) Ethyl-1,3-benzodioxole-4-carboxylate Following the procedure outlined by J. H. Clark et al, Tetrahedron Letters No. 38, 3361, 1976, ethyl-2,3-dihydroxybenzoate (4.5 g) was converted to the title compound (2.21 g, 46%).

$^1$H NMR 250 MHz ($CDCl_3$) δ: 7.42 (d, 1H), 6.98 (d, 1H), 6.86 (t, 1H), 6.11 (s, 2H), 4.40 (q, 2H), 1.40 (t, 3H).

b) 1,3-Benzodioxole-4-carboxylic acid

A solution of ethyl-1,3-benzodioxole-4-carboxylate (D13) (1 g) in water (5 ml) and ethanol (8 ml) was treated with 10% sodium hydroxide solution (3.1 mls) and heated at reflux for 30 minutes. After cooling, the reaction mixture was acidified with dilute hydrochloric acid, and the precipitate was filtered and washed with water to give the title compound (D13) (0.71 g, 84%).

$^1$H NMR 250 MHz ($d_6$-DMSO) δ: 13.01 (br s, 1H), 7.29 (d, 1H), 7.13 (d, 1H), 6.90 (t, 1H), 6.13 (s, 2H).

Description 12 (intermediate for Example 47)
a) 8-Acetamido-1,4-benzodioxan-5-(4-pyridyl)methyl carboxamide 8-Acetamido-1,4-benzodioxan-5-carboxylic acid (2.5 g) was suspended in acetonitrile (100 ml) and N,N'-carbonyl diimidazole (1.7 g) was added. The reaction mixture was stirred with gentle heating, under a nitrogen atmosphere for 1 h. The mixture was cooled to room temperature and the solvent concentrated in vacuo. The oil was filtered through a bed of silica using chloroform and ethanol as eluant. The oil was dissolved in dichloromethane (100 ml) and treated with 4-(aminomethyl)pyridine (1.17 ml). The resulting mixture was heated to reflux overnight. The solution was cooled to room temperature and the solvent removed in vacuo. The residue was chromatographed on silica eluting with ethanol/chloroform to afford pure title compound as a solid (1.47 g).

$^1$H NMR 250 MHz ($CDCl_3$) δ: 8.58(d,2H), 8.10(d, 1H), 7.92–8.00(m,1H), 7.82(d,1H), 7.69(bs, 1H), 7.28(d,2H), 4.68(d,2H), 4.39–4.47(m,4H), 2.24(s,3H)

b) 8-Acetamido-1,4-benzodioxan-5-(4-piperidyl)methyl carboxamide

A solution of 8-acetamido-1,4-benzodioxan-5-(4-pyridyl) methyl carboxamide (3.0 g) in acetic acid (200 ml) was hydrogenated at 50 psi over platinum (iv) oxide. After 4 h the catalyst was removed by filtration through keiselguhr and the flitrate concentrated in vacuo. The residue was taken up in water, basified with $K_2CO_3$ and extracted into chloroform. The organic phase was dried ($Na_2SO_4$) filtered and concentrated in vacuo to afford the title compound (2.85 g)

$^1$H NMR 250 MHz ($CDCl_3$) δ: 8.03(d,1H), 7.70–7.80(m, 2H), 7.55–7.63(m, 1H), 4.35(m,4H), 3.24(t,2H), 3.10(d,2H), 2.59(t,2H), 2.12(s,3H), 2.09(bs,1H), 1.68–1.80(m,3H), 1.11–1.29(m,2H).

c) 8-Acetamido-7-chloro-1,4-benzodioxan-5-(4-piperidyl)methyl carboxamide

A solution of 8-acetamido-1,4-benzodioxan-5-(4piperidyl)methylcarboxamide (2.56 g) in acetic acid (100 ml) was treated with a solution of chlorine (0.55 g) in acetic acid (18 ml). The reaction mixture was stirred at ambient temperature overnight. The solvent was removed in vacuo to afford the title compound as a gum (D12).

$^1$H NMR 250 MHz ($CD_3OD$) δ: 7.47(s,1H), 4.29–4.46(m, 4H), 3.29–3.49(m,4H), 3.01(t,2H), 2.12–2.21(m,3H), 1.99(s,3H), 1.43–1.62(m,2H)

Description 13 (intermediate for Example 43)
8-Acetamido-7-chloro-1,4-benzodioxan-5-(1-pentyl-4-piperidyl)methyl carboxamide To a solution of 8-acetamido-7-chloro-1,4-benzodioxan-5-(4-piperidylmethyl)carboxamide (D12) (150 mg) in acetone (15 ml) was added potassium carbonate (100 mg) and 1-bromopentane (60 μl). The resulting mixture was stirred overnight at ambient temperature. The solvent was removed in vacuo and the residue chromatographed on silica using chloroform and ethanol as eluant to afford pure product (D13) (60 mg).

¹H NMR 250 MHz (CDCl₃) δ: 7.72–7.79(s,1H), 7.55–7.65(m,1H), 7.21–7.34(m,1H), 4.32–4.50(m,4H), 3.45(t,2H), 3.03(d,2H), 2.43–2.55(t,2H), 2.15–2.29(m,3H), 2.01(t,2H), 1.21–1.82(m,11H), 0.91(t,3H)

Descriptions 14 to 16 (intermediates for Examples 44–46)

Using the procedure outlined in Description 13 the following compounds were prepared:

8-Acetamido-7-chloro-1,4-benzodioxan-5-(1-cyclohexylethyl-4-piperidyl)methyl carboxamide (D14)

¹H NMR 250 MHz (CDCl₃) δ: 7.70(s,1H), 7.47–7.55(m, 2H), 4.30–4.47(m, 4H), 3.46(t,2H), 3.01(d,2H), 2.34–2.45(m,2H), 2.21(bs,3H), 1.99(t,2H), 1.57–1.82(m, 8H), 1.09–1.49(m,8H), 0.83–1.00(m,2H)

8-Acetamido-7-chloro-1,4-benzodioxan-5-(1-isobutyl-4-piperidyl)methyl carboxamide (D15)

¹H NMR 250 MHz (CDCl₃) δ: 7.73(s,1H), 7.52–7.61(m, 1H), 7.22–7.32(m,1H), 4.32–4.49(m,4H), 3.34(t,2H), 2.91(d,2H), 2.18(bs, 3H), 2.10(d,2H), 1.52–1.97(m,6H), 1.25–1.45(m,2H), 0.89(d,6H)

8-Acetamido-7-chloro-1,4-benzodioxan-5-(1-(2-methylbutyl)-4-piperidyl)methyl-1,4-benzodioxan carboxamide (D16)

¹H NMR 250 MHz (CDCl₃) δ: 7.75(s,1H), 7.55–7.65(m, 1H), 7.19–7.30(m, 1H), 4.33–4.51(m,4H), 3.33(t,2H), 3.02(d,2H), 2.33–2.44(m,2H), 2.19(bs,3H), 2.01(t,2H), 1.37–1.81(m,8H), 0.90(d,6H)

REFERENCES

1. UK Patent 1571278
2. R. C. Fuson, R. Gaertner, A. D. H. Chadwick, J.Org.Chem. 1948, 13, 489

5-HT₄ RECEPTOR ANTAGONIST ACTIVITY

1) Guinea pig colon

Male guinea-pigs, weighing 250–400 g are used. Longitudinal muscle-myenteric plexus preparations, approximately 3 cm long, are obtained from the distal colon region. These are suspended under a 0.5 g load in isolated tissue baths containing Krebs solution bubbled with 5% $CO_2$ in $O_2$ and maintained at 37° C. In all experiments, the Krebs solution also contains methiothepin $10^{-7}$M and granisetron $10^{-6}$M to block effects at 5-HT₁, 5-HT₂ and 5-HT₃ receptors. After construction of a simple concentration-response curve with 5-HT, using 30s contact times and a 15 min dosing cycle, a concentration of 5-HT is selected so as to obtain a contraction of the muscle approximately 40–70% maximum($10^{-9}$M approx). The tissue is then alternately dosed every 15 min with this concentration of 5-HT and then with an approximately equi-effective concentration of the nicotine receptor stimulant, dimethylphenylpiperazinium (DMPP). After obtaining consistent responses to both 5-HT and DMPP, increasing concentrations of a putative 5-HT₄ receptor antagonist are then added to the bathing solution. The effects of this compound are then determined as a percentage reduction of the contractions evoked by 5-HT or by DMPP. From this data, $pIC_{50}$ values are determined, being defined as the −log concentration of antagonist which reduces the contraction by 50%. A compound which reduces the response to 5-HT but not to DMPP is believed to act as a 5-HT₄ receptor antagonist.

Compounds were generally active in the range of concentrations of the order of $pIC_{50}=7$ or more, with the compounds of Examples 1, 2, 3, 5, 6, 9, 11, 12, 21, 22, 25, 26, 27, 28, 30, 31, 32, 33, 35, 39, 40, 41, 42, 44, 49 and 53 having particularly good activity.

2) Piglet Atria

The compounds were tested in the piglet spontaneous beating atrium screen (Naunyn-Schmiedeberg's Arch. Pharmacol 342, 619–622). $pK_B$ ($-\log_{10} K_B$) values for the compounds of Examples 1, 2, 5, 10, 13, 14, 52, 53 and 55 were in the range 7 to 10.

3) Rat oesophagus

Rat oesophageal tunica muscularis mucosae was set up according to Baxter et. al. Naunyn-Schmiedeberg's Arch. Pharmacol., 343, 439–446 (1991). The inner smooth muscle tube of the muscularis mucosae was isolated and mounted for isometric tension recording in oxygenated (95% $O_2$/5% $CO_2$) Tyrodes solution at 37° C. All experiments were performed in pargyline pre-treated preparations (100 μM for 15 min followed by washout) and in the presence of cocaine (30 μM). Relaxant responses to 5-HT were obtained after pre-contracting the oesophagus tissue with carbachol (3 μM).

E1 acted as a non-surmountable antagonist of 5-HT in rat oesophagus causing as reduction in maximum response, without significant rightward displacement of concentration effect curves.

4) 5-HT-induced motility in dog gastric pouch

Compounds were tested in the in vivo method described in "Stimulation of canine motility by BRL 24924, a new gastric prokinetic agent" by Bermudez et al, J. Gastrointestinal Motility, 1990, 2(4), 281–286. Compounds showed inhibition at 10 μg kg$^{-1}$ and E1 showed inhibition at 1 μg kg$^{-1}$.

IN VIVO TESTING FOR IBS

The method is as generally described in J. Physiology, 1958, Vol. 141, p14P-15P.

Male mice (strain: CD1; weight range 25–35 g) were housed individually in perspex boxes with a mesh top and bottom for 20 min prior to dosing. Animals were then challenged with either vehicle or 5-HTP (10 mg/kg) via the subcutaneous route. Antagonists were dosed (s.c.) 5 min post-dose of saline or 5-HTP. The number of pellets was counted at 10 min. intervals for 1 hr. and finally after a further 15 mins (total time=75 min). The animals were sacrificed. The mean and SEM of the cumulative number of pellets was calculated.

E1 at 10 μg/kg had no effect on faecal pellet output when compared against saline; i.e. the compound did not constipate. 5-HTP significantly potentiated the rate of pellet output, but at this dose of 10 μg/kg whilst causing wetter pellets, did not produce diarrhoea.

E1 dose dependently inhibited the 5-HTP effect between 0.1–1 μg/kg at 1 μg/kg-100 μg/kg E1, the defaecation rate was returned to normal levels as seen with saline.

IN VIVO TESTING FOR ANXIOLYTIC ACTIVITY

1) Social Interaction

Rats (male, Sprague Dawleys, Charles River, 250–300 g) were housed in groups of eight in a holding room for 5 days. They were then housed singly in a room adjacent to the experimental room for 4 days prior to the experimental day. On the experimental day rats were administered vehicle E1 or a benzodiazepine anxiolytic, chlordiazepoxide, s.c. in pairs (n=8–16), at 15 minute intervals beginning at 10.00 a.m. 30 mins. later they were placed with a weight matched pair-mate (encountered for the first time) in the social interaction box in a separate room. The box was made of white perspex 54 cm×37 cm×26 cm with a transparent perspex front side and no lid. The floor was divided up into 24 squares and the box was brightly lit (115 lux). Active social interactive behaviours (grooming, sniffing, climbing over or under, following, biting, mounting and boxing) were scored blind for the next 15 min by remote video monitoring to give total interaction scores. The number of squares crossed by each rat was also scored and summed. After the end of each test the box was carefully wiped.

E1 increased total interaction scores over the dose range 0.001–1.0 mg/kg S.C. Locomotion scores were not significantly altered although a trend towards reduced locomotion was seen at 10.0 mg/kg S.C. This profile is consistent with anxiolysis.

2) X-Maze

The X-maze was raised 50 cm above the floor and consisted of two enclosed arms 45 cm (long)×10 cm (wide) and 10 cm (high) and two open arms 45×10×1 cm, arranged such that the two arms of each type were opposite each other. Both arm types were marked into two equal sections. Rats were placed onto the centre of the X-maze and observed for a period of five min during which time the following parameters were recorded: 1) The number of entries on to, and the time spent on, (a) open arms (b) closed arms, (c) end of open arms and (d) end of closed arms. 2) the number of sections crossed. The fear drive evoked in the open arms exceeds that in the closed arms and rats typically show a clear preference for the enclosed arms. Anxiolytic drugs increase the number of entries made onto, and the time spent on, the outer half of the open arms, and also the percentage of entries made onto, and the time spent on, the whole of the open arms. These four measures of anxiety, and also the total number of sections traversed, were calculated for each animal.

At doses between 0.01 and 1.0 mg/kg s.c., E1 increased measures of anxiolysis (time spent on open arm, entries to end of open arm, % time on open am and % entries onto open arm), without affecting locomotion over a five minute period. The most consistently affected measure was % time on the open arm. This profile of action is consistent with anxiolysis and was mirrored by the positive control, chlordiazepoxide (5 mg/kg s.c.).

IN VIVO TESTING FOR ANTIEMETIC ACTIVITY

Ferrets were dosed 10 μg kg$^{-1}$ p.o., 15 min before total body irradiation (Bermudez et al, Br J. Cancer 1988, 58, p644)

|  | MEAN NO. VOMITS | MEAN NO. RETCHES |
|---|---|---|
| Control n = 8 | 14 ± 1.6 | 120.3 ± 16.1 |
| E1 | 6.3 ± 1.6 | 81.5 ± 11.6 |

Data: Mean ± sem

We claim:

1. A compound of the formula:

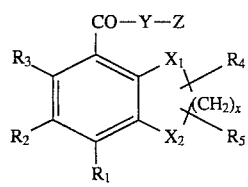

wherein:

$X_1$ is O or S;

$X_2$ is O or S;

x is 1, 2 or 3;

$R_1$ is hydrogen, amino, halo, $C_{1-6}$alkyl, hydroxy or $C_{1-6}$alkoxy;

$R_2$ is hydrogen, halo, $C_{1-6}$alkyl, $C_{1-6}$alkoxy, nitro, amino or $C_{1-6}$alkylthio;

$R_3$ is hydrogen, halo, $C_{1-6}$alkyl, $C_{1-6}$alkoxy or amino;

$R_4$ and $R_5$ are independently hydrogen or $C_{1-6}$ alkyl;

Y is O, and Z is of sub-formula (a), (b) or (c):

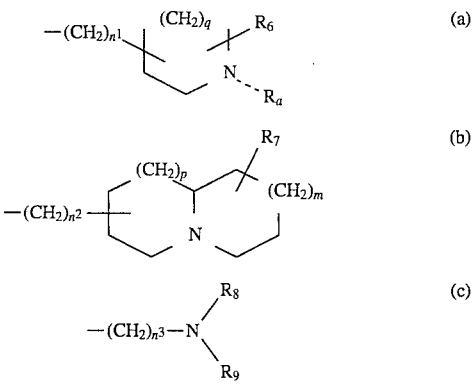

wherein

—$(CH_2)_n{}^1$ is attached at carbon or nitrogen and $n^1$ is 1, 2, 3 or 4;

$n^2$ is 1 or 2;

$n^3$ is 2, 3, 4 or 5;

q is 0, 1, 2 or 3;

p is 0, 1 or 2;

m is 0, 1 or 2;

$R_a$ is hydrogen, $C_{1-10}$alkyl or aralkyl;

$R_6$, $R_7$ and $R_8$ are independently hydrogen or $C_{1-6}$alkyl; and $R_9$ is hydrogen or $C_{1-10}$alkyl;

or a pharmaceutically acceptable salt thereof.

2. A compound according to claim 1 wherein $X_1$—$(CH_2)_x$—$X_2$ is O—$(CH_2)_2$—O.

3. A compound selected from:

8-amino-7-chloro-(1-butyl-4-piperidyl)methyl-1,4-benzodioxan-5-carboxylate, 8-amino-(1-butyl-4-piperidyl)methyl-1,4-benzodioxan-5-carboxylate, 7-bromo-5-(1-butyl-4-piperidyl)methyl-1,4-benzodioxan-5-carboxylate, (1-butyl-4-piperidyl)methyl-1,4-benzodioxan-5-carboxylate, 7-chloro-(1-butyl-4-piperidyl)methyl-1,4-benzodioxan-5-carboxylate, 8-amino-6,7-dichloro-(1-butyl-4-piperidyl)methyl-1,4-benzodioxan-5-carboxylate, 8-amino-7-iodo-(1-cyclohexylmethyl-4-piperidyl)methyl-1,4-benzodioxan-5-carboxylate, 8-amino-7-chloro-1,4-benzodioxan-(αx-3-quinolizidinyl) methyl carboxylate, 8-amino-7-chloro-1,4-benzodioxan-(eq-3-quinolizidinyl) methyl carboxylate, 8-amino-7-chloro-(1-cyclohexylmethyl-4-piperidyl)methyl-1,4-benzodioxan-5-carboxylate, eq-quinolizidin-2-ylmethyl-7-chloro-1,4-benzodioxan-5-carboxylate, or eq-quinolizidin-2-ylmethyl-8-amino-7-chloro-1,4-benzodioxan-5-carboxylate, in free base form, or as a pharmaceutically acceptable salt.

4. A pharmaceutical composition comprising a compound according to claim 1, and a pharmaceutically acceptable carrier.

5. A method of treating irritable bowel syndrome, atrial arrhythmia, or stroke, comprising administering an effective amount of a compound according to claim 1.

* * * * *